United States Patent
Taylor et al.

(10) Patent No.: US 10,292,743 B2
(45) Date of Patent: May 21, 2019

(54) SURGICAL STAPLE

(71) Applicant: Wright Medical Technology, Inc., Memphis, TN (US)

(72) Inventors: Alan G. Taylor, Memphis, TN (US); Rebecca H. Wahl, Escondido, CA (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 13/782,274

(22) Filed: Mar. 1, 2013

(65) Prior Publication Data
US 2013/0231667 A1 Sep. 5, 2013

Related U.S. Application Data

(60) Provisional application No. 61/605,269, filed on Mar. 1, 2012, provisional application No. 61/642,353, filed on May 3, 2012.

(51) Int. Cl.
A61B 17/84 (2006.01)
A61B 17/064 (2006.01)
(Continued)

(52) U.S. Cl.
CPC .......... *A61B 17/84* (2013.01); *A61B 17/0642* (2013.01); *A61B 17/8004* (2013.01);
(Continued)

(58) Field of Classification Search
CPC .............. A61B 17/064; A61B 17/0642; A61B 17/8004; A61B 17/809; A61B 2017/0645
(Continued)

(56) References Cited

U.S. PATENT DOCUMENTS 3,988,783 A * 11/1976 Treace ..................... A61F 2/08
623/13.14
5,785,713 A 7/1998 Jobe
(Continued)

FOREIGN PATENT DOCUMENTS

CN 101106949 A 1/2008
EP 0548998 A1 6/1993
(Continued)

OTHER PUBLICATIONS

Amazon ("Gardner Bender PS-175ZN Plastic Staple, ¾ Inch, Secures Romex, UF & (NM) Non-Metalic Cable, Polyethylene—UV Resistant, Splinter Free, Application: 14/3, 12/3, 10/3 (NM) Cable, 100 Pk, White—Hardware Staples." Amazon, Amazon, www.amazon.com/dp/B000BQNBQ8/ref=sspa_dk_detail_1?psc=1 &pd_rd_i=B000BQNBQ8&pd_rd_wg=jsMXK&pd_rd_r= 9WAFMRGGW8BFZA.*
(Continued)

*Primary Examiner* — Kevin T Truong
*Assistant Examiner* — Marcela I Shirsat
(74) *Attorney, Agent, or Firm* — Duane Morris LLP

(57) ABSTRACT

A surgical staple (714) for inserting into one or more bone parts (10, 12) comprises a plate (718), a first screw (748) and a second screw (748). The plate (718) includes a first end (768F), an opposed second end (768S), a first aperture (742) that is positioned near the first end (768F), and a second aperture (742) that is positioned near the second end (768S). Additionally, the plate (718) is curved along a length of the plate (718) from the first end (768F) to the second end (768S). The first screw (748) extends through the first aperture (742). The second screw (748) extends through the second aperture (742). Further, the first screw (748) and the second screw (748) are angled toward one another when the surgical staple (714) is in a relaxed configuration.

20 Claims, 7 Drawing Sheets

(51) Int. Cl.
*A61B 17/80* (2006.01)
*A61B 17/00* (2006.01)

(52) U.S. Cl.
CPC ........ *A61B 17/809* (2013.01); *A61B 17/8085* (2013.01); *A61B 2017/00862* (2013.01); *A61B 2017/00867* (2013.01); *A61B 2017/0645* (2013.01)

(58) Field of Classification Search
USPC ....... 606/71, 75, 76, 78, 151, 219, 280, 286, 606/297, 300, 311, 324, 326, 327, 329, 606/330, 331, 157, 221, 283, 284, 606/298–299; 128/831, 834
See application file for complete search history.

(56) References Cited

U.S. PATENT DOCUMENTS

| | | | |
|---|---|---|---|
| 6,187,009 B1 * | 2/2001 | Herzog | A61B 17/68 606/232 |
| 6,290,703 B1 | 9/2001 | Ganem | |
| 6,325,805 B1 * | 12/2001 | Ogilvie et al. | 606/75 |
| 7,344,539 B2 * | 3/2008 | Serhan | A61B 17/0642 606/247 |
| 7,635,364 B2 | 12/2009 | Barrall et al. | |
| 2002/0120270 A1 * | 8/2002 | Trieu | A61F 2/08 623/13.11 |
| 2004/0087951 A1 | 5/2004 | Khalili | |
| 2007/0166122 A1 * | 7/2007 | McDuff | F16B 13/0808 411/31 |
| 2008/0161808 A1 * | 7/2008 | Fox | A61B 17/0642 606/75 |
| 2009/0062800 A1 * | 3/2009 | Shano | 606/75 |
| 2009/0275947 A1 * | 11/2009 | Graham et al. | 606/71 |
| 2009/0287249 A1 * | 11/2009 | Reynolds et al. | 606/246 |
| 2010/0125301 A1 | 5/2010 | Kinmon et al. | |
| 2011/0118842 A1 * | 5/2011 | Bernard | A61B 17/0642 623/17.11 |
| 2012/0209338 A1 * | 8/2012 | Groiso | A61B 17/0642 606/331 |

FOREIGN PATENT DOCUMENTS

| | | |
|---|---|---|
| FR | 2916954 A1 | 12/2008 |
| WO | WO9217122 A2 | 10/1992 |
| WO | WO2008149308 A1 | 12/2008 |
| WO | WO2009091770 A1 | 7/2009 |
| WO | WO2010010522 A1 | 1/2010 |

OTHER PUBLICATIONS

Stryker (Stryker. "Staple Fixation System—Stryker." 2007, viewed on www.yumpu.com/en/document/view/25072096/staple-fixation-system-stryker., last accessed Jun. 7, 2018).*
The International Search Report of the International Searching Authority, dated Aug. 28, 2013 for Application No. PCT/US2013/028627 (related application).
The Written Opinion of the International Searching Authority, dated Aug. 28, 2013 for Application No. PCT/US2013/028627 (related application).
European Patent Office, Invitation to Pay Additional Fees, dated Jun. 7, 2013 for Application No. PCT/US2013/028627 (related application).
First Office Action dated Dec. 16, 2015, in corresponding Chinese patent application No. 201380011338.0, 10 pages.
Second Office Action dated Aug. 10, 2016, in corresponding Chinese patent application No. 201380011338.0, 10 pages.
Third Office Action dated Jan. 19, 2017, in corresponding Chinese patent application No. 201380011338.0, 11 pages.
Office Action issued in connection with corresponding European patent application No. 13710223.2, dated Jul. 3, 2017, 5 pages.

* cited by examiner

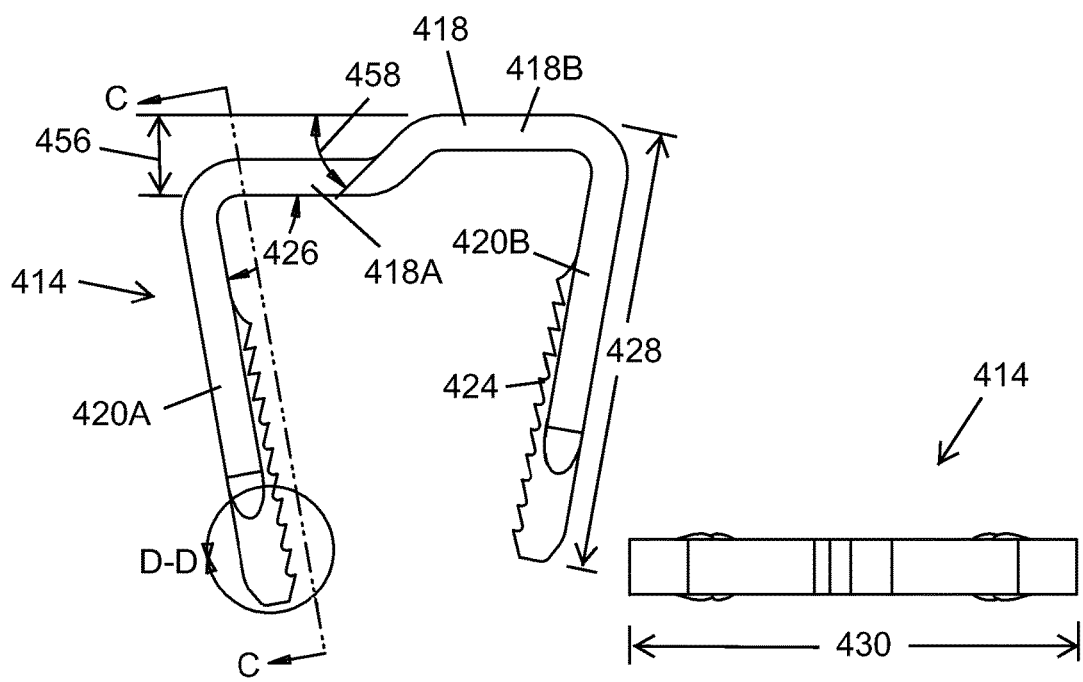
FIG. 4A
FIG. 4B
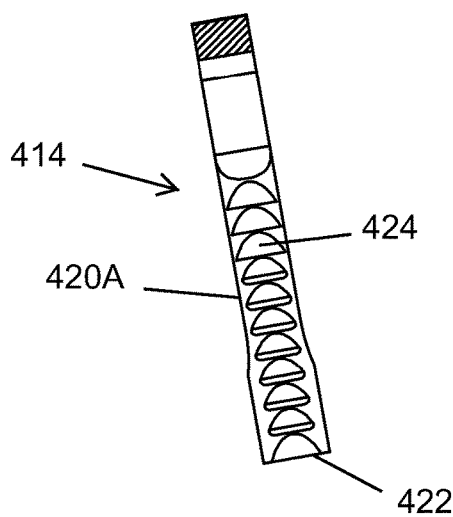
FIG. 4C
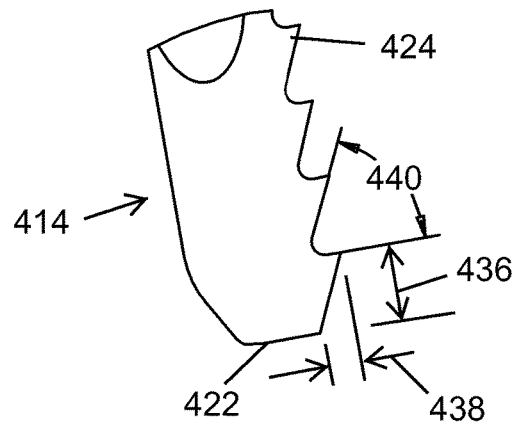
FIG. 4D

SURGICAL STAPLE

RELATED INVENTION

This application claims priority on U.S. Provisional Application Ser. No. 61/605,269, filed Mar. 1, 2012 and entitled "SURGICAL STAPLE"; and U.S. Provisional Application Ser. No. 61/642,353, filed May 3, 2012 and entitled "SURGICAL STAPLE". As far as permitted, the contents of U.S. Provisional Application Ser. Nos. 61/605,269 and 61/642,353 are incorporated herein by reference.

BACKGROUND

Surgical staples are often utilized for closure of the skin in a wide variety of surgical procedures. Additionally, surgical staples can be utilized to move and/or maintain bones or bone parts substantially adjacent to one another after certain surgical procedures. Moreover, surgical staples are often utilized to compress and hold together in place two displaced pieces of bone while healing. Often a hole or holes are necessary in the bone material for proper insertion of the surgical staples. It is desired that the surgical staples provide the necessary force distribution to inhibit leakage.

SUMMARY

In one application, the present invention is directed toward a surgical staple for inserting into one or more bone parts, the surgical staple being selectively movable between a relaxed configuration and an opened configuration. In certain embodiments, the surgical staple comprises a plate, a first screw and a second screw. The plate includes a first end, an opposed second end, a first aperture that is positioned near the first end, and a second aperture that is positioned near the second end. Additionally, the plate is curved along a length of the plate from the first end to the second end. The first screw extends through the first aperture. The second screw extends through the second aperture. Further, the first screw and the second screw are angled toward one another when the surgical staple is in the relaxed configuration.

In one embodiment, the plate has an angle of curvature of between approximately 16.0 and 26.0 degrees. Additionally and/or alternatively, in one embodiment, the plate includes a center that is positioned between and spaced apart form the first end and the second end, and the plate has a plate deflection from the center to the first end of between approximately 2.0 and 3.0 millimeters.

In some embodiments, the surgical staple further comprises a first side section and a second side section that cantilever away from the plate, the first side section cantilevering away from the plate near the first end, and the second side section cantilevering away from the plate near the second end. In one such embodiment, the first screw extends through the first side section, and the second screw extends through the second side section. Additionally, in certain such embodiments, the first side section and the second side section are angled toward one another when the surgical staple is in the relaxed configuration. In one such embodiment, the first side section cantilevers away from the plate at a leg angle of between approximately 75.0 and 85.0 degrees when the surgical staple is in the relaxed configuration.

Further, in certain embodiments, the plate is made from a resilient material

Additionally, in another application, the present invention is directed toward a surgical staple for inserting into one or more bone parts, the surgical staple being selectively movable between a relaxed configuration and an opened configuration, the surgical staple comprising (i) a middle section; and (ii) a first side section that cantilevers away from the middle section, the first side section including an upper portion that is positioned substantially adjacent to the middle section and an end that is positioned away from the middle section, wherein the end is at least approximately five percent wider than the upper portion.

Further, in still another application, the present invention is directed toward a method for compressing a first bone part and a second bone part, the method comprising the steps of (i) positioning a plate substantially adjacent to at least one of the first bone part and the second bone part, the plate including a first end, an opposed second end, a first aperture that is positioned near the first end, and a second aperture that is positioned near the second end, the plate being curved along a length of the plate from the first end to the second end, and the plate being selectively movable between a relaxed configuration and an opened configuration; (ii) extending a first screw through the first aperture and into the first bone part; and (iii) extending a second screw through the second aperture and into the second bone part, the first screw and the second screw being angled toward one another when the plate is in the relaxed configuration.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 4A is a simplified front view of still another embodiment of a surgical staple having features of the present invention;

FIG. 4B is a simplified top view of the surgical staple of FIG. 4A;

FIG. 4C is a sectional view of the surgical staple taken on line C-C in FIG. 4A;

FIG. 4D is an enlarged view of a portion of the surgical staple as indicated by circle and arrows D-D in FIG. 4A;

DESCRIPTION

Figure 1:
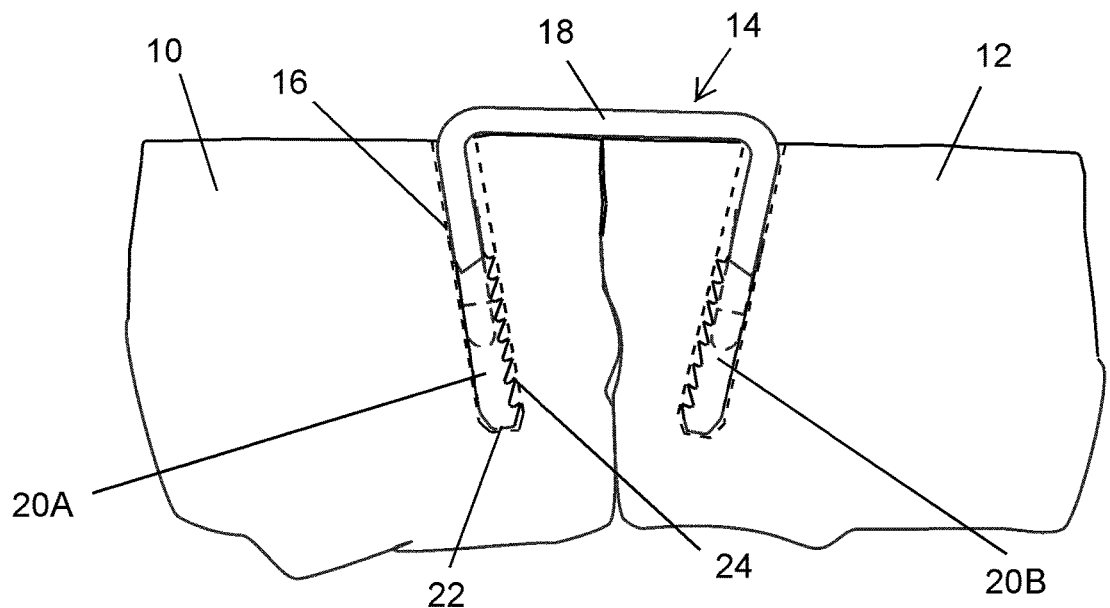
FIG. 1 is a simplified schematic illustration of a first bone part, a second bone part, and an embodiment of a surgical staple having features of the present invention that can be utilized to hold the bone parts together.

FIG. 1 is a simplified schematic illustration of a first bone part 10, a second bone part 12, and an embodiment of a surgical staple 14 having features of the present invention that can be utilized to hold the bone parts 10, 12 together.

In certain applications, prior to insertion of the surgical staple 14, the bone parts 10, 12 can be prepared by drilling or otherwise forming a hole 16 (illustrated in phantom) in each of the bone parts 10. Subsequently, the surgical staple 14 can be inserted as desired with a portion of the surgical staple 14 being effectively and securely positioned within the hole 16 in each of the bone parts 10, 12. Additionally, the surgical staple 14 can be used for certain desired purposes, e.g., for closure of the skin adjacent to the bone parts 10, 12, for moving and/or maintaining the bone parts 10, 12 substantially adjacent to one another, and/or for compressing and holding together in place the bone parts 10, 12 while healing. Additionally and/or alternatively, the surgical staple 14 can be utilized for other suitable purposes.

The design of the surgical staple 14 can be varied. As illustrated, in certain embodiments, the surgical staple 14 can be somewhat horseshoe shaped, and the surgical staple 14 can include a substantially flat middle section 18 and two side sections, i.e. a first side section 20A and a second side section 20B, that cantilever away from the middle section 18. Alternatively, in certain embodiments, the middle section 18 can be curved or arched.

Additionally, in some embodiments, the surgical staple 14 is selectively movable between a relaxed configuration and an opened configuration, with the surgical staple 14 having resilient properties such that the surgical staple 14 is biased to return and/or move toward the relaxed configuration. When in the relaxed configuration, each of the side sections 20A, 20B can cantilever away from the middle section 18 at an angle of less than ninety degrees such that the side sections 20A, 20B are angled slightly toward one another. Conversely, when in the opened configuration, each of the side sections 20A, 20B can cantilever away from the middle section 18 at an angle of closer to ninety degrees, e.g., approximately ninety degrees in one such embodiment. In such embodiments, during use, the surgical staple 14 can be moved from the relaxed configuration to the opened configuration manually, automatically, and/or with the use of a tool, and the surgical staple 14 can be inserted into the holes 16 in the bone parts 10, 12 when the surgical staple is in the opened configuration. After insertion, the bias of the surgical staple 14 causes the side sections 20A, 20B to move somewhat (or at least try to move depending on the specific orientation of the holes 16) toward one another, i.e. toward the relaxed configuration. With this design, the surgical staple 14 can be maintained securely within the holes 16, and the side sections 20A, 20B can provide improved compressing and holding together of the bone parts 10, 12 during the healing process.

Further, each side section 20A, 20B can have an end 22 that is somewhat tapered such that the end 22 is narrower in cross-section (i.e. in at least one direction) than the majority of the side section 20A, 20B to better enable insertion of the surgical staple 14 into the bone parts 10, 12. Further, the side sections 20A, 20B of the surgical staple 14 can include a plurality of teeth 24 that are angled so as to enable easy insertion of the surgical staple 14, while also inhibiting removal of the surgical staple 14 from the bone parts 10, 12.

As an overview, with the design of the surgical staple 14 as illustrated and described herein, the surgical staple 14 can achieve certain desired benefits. For example, the angling of the side sections 20A, 20B toward one another while in the relaxed configuration, as well as the arch or curvature of the middle section 18 (in certain embodiments) help to provide better holding together and compression between the bone parts 10, 12 during the healing process. Additionally, the side sections 20A, 20B of the surgical staple 14 can have a wider foot design, which also helps to enable the realization of certain benefits. More particularly, the wider foot design of the side sections 20A, 20B enables (i) more complete filling of the holes 16 in the bone parts 10, 12 by the side sections 20A, 20B; (ii) better force distribution against the bone material within the bone parts 10, 12 due to the larger surface area of the side sections 20A, 20B; (iii) better bone to bone compression as a result of the better force distribution, because the side sections 20A, 20B can move the bone parts 10, 12 together more effectively than just cutting into the bone; and (iv) moving the bone parts 10, 12 a greater distance with the side sections 20A, 20B as a result of the more complete filling of the holes 16 to further provide better compression.

Moreover, as noted above, the unique design of the teeth 24 enables easy insertion of the surgical staple 14, i.e. the side sections 20A, 20B, into the holes 16 in the bone parts 10, 12, while inhibiting removal of the surgical staple 14 from the bone parts 10, 12 after insertion.

Further, in one embodiment, the surgical staple 14 can be formed from a nitinol superelastic material. Alternatively, the surgical staple 14 can be made from another appropriately resilient, flexible and/or elastic material. Moreover, as illustrated, the surgical staple 14 can have a unitary construction such that the surgical staple 14 can be formed from a single piece of nitinol superelastic material, or other appropriate material. With this design, the connections between the middle section 18 and each of the side sections 20A, 20B can be somewhat rounded, thereby inhibiting potential discomfort for the patient into whom the surgical staple 14 is inserted. Alternatively, the surgical staple 14 can be made of individual sections that are secured together.

Figure 2A:
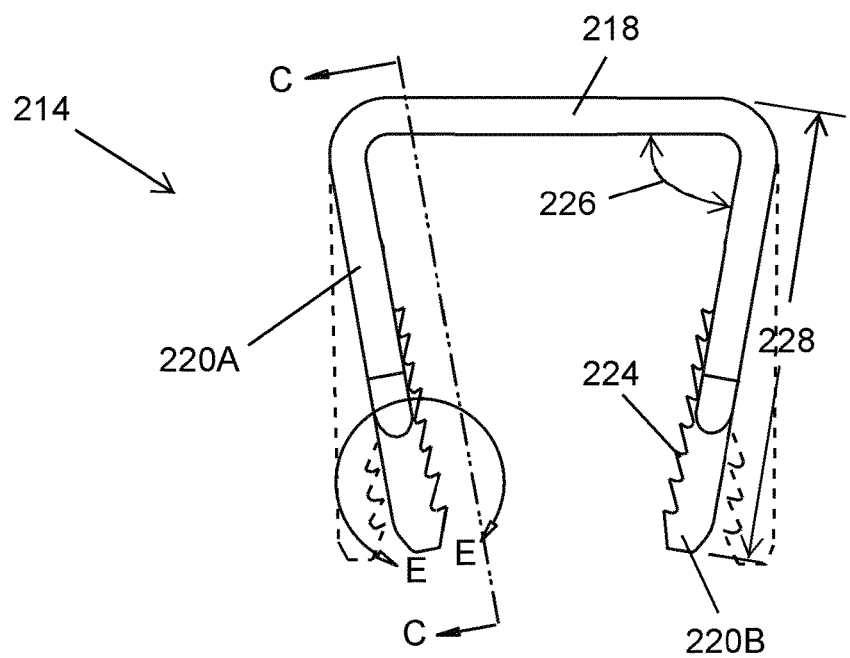
FIG. 2A is a simplified front view of an embodiment of a surgical staple having features of the present invention.

FIG. 2A is a simplified front view of an embodiment of a surgical staple 214 having features of the present invention. The design and size of the surgical staple 214 can be varied to suit the specific requirements of the procedure being performed and/or the patient with whom the surgical staple 214 is being used. As illustrated in this embodiment, the surgical staple 214 is again somewhat horseshoe shaped, and the surgical staple 214 again includes a substantially flat middle section 218 and two side sections, i.e. a first side section 220A and a second side section 220B, that cantilever away from the middle section 218. Alternatively, the surgical staple 214 can have a different design. For example, in one embodiment, the middle section 218 can be other than substantially flat, e.g., the middle section 218 can be curved or arched.

Additionally, the surgical staple 214 can be formed from a nitinol superelastic material, or another appropriately resilient, flexible and/or elastic material, such that the surgical staple 214 is selectively movable between a relaxed configuration (illustrated in solid lines FIG. 2A) and an opened configuration (illustrated in phantom in FIG. 2A). As shown in FIG. 2A, when the surgical staple 214 is in the relaxed configuration, each of the side sections 220A, 220B cantilevers away from the middle section 218 at a leg angle 226 that is less than ninety degrees, such that the side sections 220A, 220B are angled slightly toward one another. Further, the leg angle 226 between one side section 220A and the middle section 218 can be substantially the same or can be different than the leg angle 226 between the other side section 220B and the middle section 218. In particular, in certain embodiments, each of the side sections 220A, 220B can cantilever away from the middle section 218 at a leg angle 226 of between approximately 75.0 and 85.0 degrees. For example, in certain non-exclusive alternative embodiments, the leg angle 226 between the side sections 220A, 220B and the middle section 218 can be approximately 75.0, 77.0, 79.0, 80.0, 81.0, 83.0 or 85.0 degrees. Alternatively, the leg angle 226 can be greater than 85.0 degrees, less than 75.0 degrees, or another value between 75.0 and 85.0 degrees.

When the surgical staple 214 is in the opened configuration, the side sections 220A, 220B can cantilever away from the middle section 218 at a leg angle 226 of closer to or approximately ninety degrees. In such configuration, the surgical staple 214 can be quickly and easily inserted into the holes 16 (illustrated in FIG. 1) that have been created in the bone parts 10, 12 (illustrated in FIG. 1) to specifically receive the surgical staple 214. For example, in certain applications, when the surgical staple 214 is in the opened configuration, each of the side sections 220A, 220B can cantilever away from the middle section 218 at a leg angle 226 of approximately 95.0, 94.0, 93.0, 92.0, 91.0, 90.0, 89.0, 88.0, 87.0, 86.0, or 85.0 degrees, or at some other leg angle 226.

Further, as illustrated in FIG. 2A, each of the side sections 220A, 220B has a leg length 228. The leg length 228 of each of the side sections 220A, 220B can be varied. In some embodiments, each of the side sections 220A, 220B can have a leg length 228 of between approximately 8.0 and 12.0 millimeters. For example, in certain non-exclusive alternative embodiments, the leg length 228 can be approximately, 8.0, 9.0, 10.0, 11.0 or 12.0 millimeters. Alternatively, the leg length 228 can be greater than 12.0 millimeters, less than 8.0 millimeters, or some other value between 8.0 and 12.0 millimeters.

Moreover, in certain embodiments, the surgical staple 214 can again include a plurality of teeth 224 that are fixedly secured to and/or integrally formed with each of the side sections 220A, 220B. As described above, the teeth 224 are sized and shaped to enable easy insertion of the surgical staple 214, while inhibiting removal of the surgical staple 214 from the bone parts 10, 12 (illustrated in FIG. 1) after insertion.

The number and size of the teeth 224 can be varied. In some embodiments, the surgical staple 214 can include between approximately three and twelve teeth 224 that are fixedly secured to and/or integrally formed with each of the side sections 220A, 220B. For example, in certain non-exclusive alternative embodiments, the surgical staple 214 can include three, four, five, six, seven, eight, nine, ten, eleven or twelve teeth 224 that are fixedly secured to and/or integrally formed with each of the side sections 220A, 220B. Alternatively, each of the side sections 220A, 220B can be designed to have greater than twelve or less than three teeth 224.

Figure 2B:
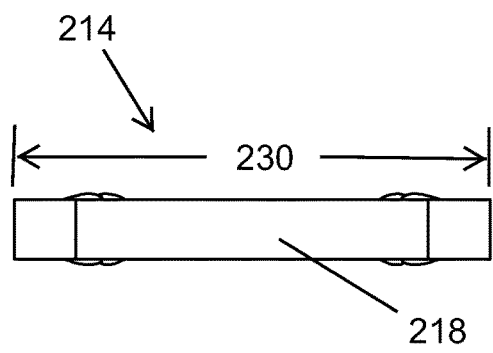
FIG. 2B is a simplified top view of the surgical staple of FIG. 2A.

FIG. 2B is a simplified top view of the surgical staple 214 of FIG. 2A. FIG. 2B illustrates certain additional features of this embodiment of the surgical staple 214. For example, as shown in FIG. 2B, the surgical staple 214 has a staple width 230, which, as measured, is substantially equivalent to the length of the middle section 218 of the surgical staple 214. Additionally, in some embodiments, the staple width 230 can be substantially equal to the leg length 228 (illustrated in FIG. 2A) of each of the side sections 220A, 220B (illustrated more clearly in FIG. 2A). In certain embodiments, the surgical staple 214 can have a staple width 230 of between approximately 8.0 and 12.0 millimeters. For example, in certain non-exclusive alternative embodiments, the staple width 230 can be approximately, 8.0, 9.0, 10.0, 11.0 or 12.0 millimeters. Alternatively, the staple width 230 can be greater than 12.0 millimeters, less than 8.0 millimeters, or some other value between 8.0 and 12.0 millimeters.

Figure 2C:
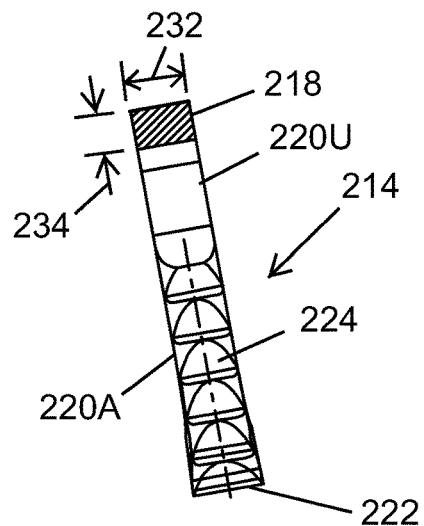
FIG. 2C is a sectional view of the surgical staple taken on line C-C in FIG. 2A.

FIG. 2C is a sectional view of the surgical staple 214 taken on line C-C in FIG. 2A. In particular, FIG. 2C illustrates still further details of the surgical staple 214. For example, FIG. 2C illustrates the general cross-sectional shape of the surgical staple 214, i.e. of the middle section 218 of the surgical staple 214. As shown, in certain embodiments, the surgical staple 214 can have a generally rectangular cross-section. In particular, in such embodiments, the surgical staple 214 can include a body width 232 and a body thickness 234. In some embodiments, the surgical staple 214 can have a body width 232 of between approximately 1.0 and 2.0 millimeters, and a body thickness 234 of between approximately 0.8 and 1.6 millimeters. For example, in one non-exclusive alternative embodiment, the surgical staple 214 can have a body width 232 of approximately 1.5 millimeters and a body thickness 234 of approximately 1.2 millimeters. Alternatively, the surgical staple 214 can have a body width 232 that is greater than 2.0 millimeters or less than 1.0 millimeters, and/or the surgical staple 214 can have a body thickness 234 that is greater than 1.6 millimeters or less than 0.8 millimeters.

Additionally, as illustrated, the end 222 of the side sections (only the first side section 220A is illustrated in FIG. 2C) flares outwardly slightly relative to the majority of the side section 220A and/or relative to the body width 232. Stated in another manner, the side section 220A has a wider end 222 (or foot) design that enables the side section 220A to fill the hole 16 (illustrated in FIG. 1) more completely in the bone part, e.g., the first bone part 10 or the second bone part 12 illustrated in FIG. 1. In certain embodiments, the end 222 can be wider than an upper portion 220U of the side section 220A (i.e. adjacent to the middle section 218) by between approximately 5.0 and 15.0 percent. For example, in certain non-exclusive alternative embodiments, the end 222 can be at least approximately 5.0, 6.0, 7.0, 8.0, 9.0, 10.0, 11.0, 12.0, 13.0, 14.0 or 15.0 percent wider than the upper portion 220U of the side section 220A. Alternatively, the end 222 can be greater than 15.0 percent, less than 5.0 percent, or some other value between 5.0 and 15.0 percent wider that the upper portion 220U of the side section 220A. Moreover, as noted above, such design further enables better force distribution against the bone part 10, 12, and greater movement of the bone part 10, 12, which, in turn, results in better bone to bone compression.

Further, FIG. 2C also illustrates the general shape of the teeth 224 that are fixedly secured to and/or integrally formed with each of the side sections 220A. For example, as shown in FIG. 2C, each of the teeth 224 tapers inwardly toward the top of the tooth 224.

Figure 2D:
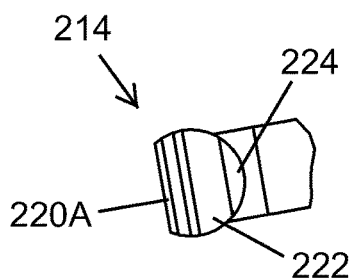
FIG. 2D is a simplified bottom view of a portion of the surgical staple of FIG. 2A.

FIG. 2D is a simplified bottom view of a portion of the surgical staple 214 of FIG. 2A. More specifically, FIG. 2D more clearly illustrates certain design aspects of the end 222 of the side section 220A. Additionally, FIG. 2D further illustrates that in certain embodiments, the teeth 224 can have a rounded profile as the teeth 224 extend away from the remainder of the side section 220A.

Figure 2E:
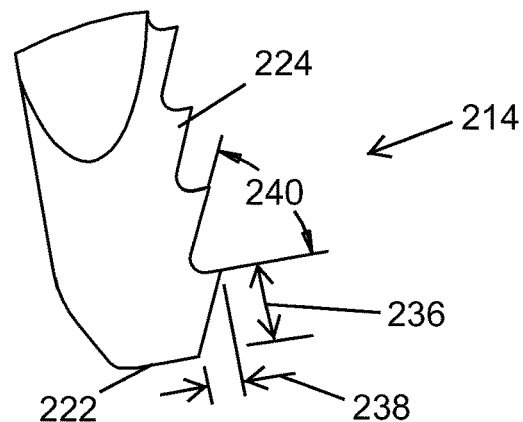
FIG. 2E is an enlarged view of a portion of the surgical staple as indicated by circle and arrows E-E in FIG. 2A.

FIG. 2E is an enlarged view of a portion of the surgical staple 214 as indicated by circle and arrows E-E in FIG. 2A. In particular, FIG. 2E more clearly illustrates certain design aspects of the teeth 224 that are fixedly secured to and/or integrally formed with the side section 220A. For example, FIG. 2E illustrates a tooth height 236, a tooth depth 238 and a tooth angle 240 of the teeth 224.

In certain embodiments, the tooth height 236 can be between approximately 1.00 and 1.30 millimeters. For example, in certain non-exclusive alternative embodiments, the tooth height 236 can be approximately 1.00, 1.05, 1.10, 1.15, 1.20, 1.25 or 1.30 millimeters. Alternatively, the tooth height 236 can be greater than 1.30 millimeters, less than 1.00 millimeters, or some other value between 1.00 and 1.30 millimeters.

Additionally, in certain embodiments, the tooth depth 238 can be between approximately 0.30 and 0.50 millimeters. For example, in certain non-exclusive alternative embodiments, the tooth depth 238 can be approximately 0.30, 0.35, 0.40, 0.45 or 0.50 millimeters. Alternatively, the tooth depth 238 can be greater than 0.50 millimeters, less than 0.30 millimeters, or some other value between 0.30 and 0.50 millimeters.

Further, in certain embodiments, the tooth angle 240 can be between approximately 60.0 and 80.0 degrees. For example, in certain non-exclusive alternative embodiments, the tooth angle 240 can be approximately 60.0, 62.5, 65.0, 67.5, 70.0, 72.5, 75.0, 77.5 or 80.0 degrees. Alternatively, the tooth angle 240 can be greater than 80.0 degrees, less than 60.0 degrees, or some other value between 60.0 and 80.0 degrees.

Still further, FIG. 2E also illustrates that the end 222 of the side section 220A can be narrower in cross-section than the majority of the side section 220A to better enable insertion of the surgical staple 214 into the bone parts 10, 12 (illustrated in FIG. 1).

Figure 3A:
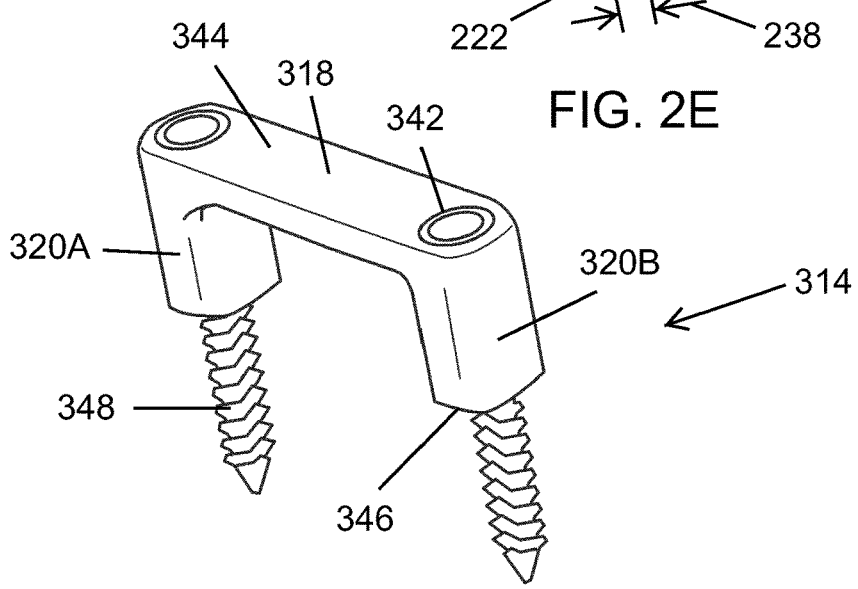
FIG. 3A is a simplified perspective view of another embodiment of a surgical staple having features of the present invention.

FIG. 3A is a simplified perspective view of another embodiment of a surgical staple 314 having features of the present invention. As illustrated, the surgical staple 314 illustrated and described in FIG. 3A is somewhat similar to the surgical staple 214 illustrated and described above in relation to FIGS. 2A-2E. For example, the surgical staple 314 again includes a substantially flat middle section 318 and two side sections 320A, 320B that cantilever away from the middle section 318. Additionally, as in the previous embodiment, the surgical staple 314 can be selectively movable between a relaxed configuration (as illustrated, for example, in FIG. 3B) and an opened configuration (as illustrated in FIG. 3C). More specifically, when the surgical staple 314 is in the relaxed configuration, the side sections 320A, 320B can again cantilever away from the middle section 318 at an angle of less than ninety degrees such that the side sections 318 are angled slightly toward one another. In some embodiments, the side sections 320A, 320B can also include one or more teeth (not illustrated) that are fixedly secured to and/or integrally formed with each of the side sections 320A, 320B.

In this embodiment, the middle section 318 is substantially narrow plate shaped. Additionally, in this embodiment, the surgical staple 314 includes a pair of screw apertures 342 that extend through a top surface 344 of the middle section 318 of the surgical staple 314 and through the length of the side sections 320A, 320B such that the screw aperture 342 extends through an end 346 of the side section 320A, 320B away from the middle section 318. Each of the screw apertures 342 is adapted to receive a screw 348 that is designed to be inserted into one of the holes 16 (illustrated in FIG. 1) in the bone parts 10, 12 (illustrated in FIG. 1). More specifically, as shown in FIG. 3A, each of the screws 348 is threaded and/or extended fully through the corresponding screw aperture 342 such that the screw 348 extends outwardly beyond the end 346 of the side section 320A, 320B. With this design, the side sections 320A, 320B can extend part way into the depth of the holes 16 in the bone parts 10, 12, and the screws 348 can be threaded further into the holes 16 in the bone parts 10, 12 so that the surgical staple 314 is more securely retained within the holes 16 in the bone parts 10, 12.

Additionally, as with the surgical staple 214 illustrated and described above in relation to FIGS. 2A-2E, in one embodiment, the surgical staple 314 can be formed from a nitinol superelastic material. Alternatively, the surgical staple 314 can be made from another appropriately resilient, flexible and/or elastic material. Further, as illustrated, the surgical staple 314 can have a unitary construction such that the surgical staple 314 is formed from a single piece of nitinol superelastic material, or other appropriate material. With this design, the connections between the middle section 318 and each of the side sections 320A, 320B can be slightly rounded. Alternatively, the surgical staple 314 can be made of individual sections that are secured together.

With the design of the surgical staple 314 as illustrated and described herein, the surgical staple 314 can achieve certain desired benefits. For example, (i) the nitinol superelastic plate, i.e. middle section 318, combines the rigidity of a plate with the compression of a superelastic staple; (ii) such a surgical staple 314 can utilize either locking or non-locking screws 348; (iii) the surgical staple 314 is placed similar to placing a more traditional staple, i.e. by using a drill guide, with an inserter holding the side sections 320A, 320B substantially straight during insertion; (iv) the screws 348 inserted down through the screw apertures 342 in the side sections 320A, 320B improve the strength and stability characteristics of the surgical staple 314; (v) the surgical staple 314 can include up to six screw apertures 342 is certain alternative embodiments to accommodate different size requirements; and (vi) the surgical staple 314 can be manufactured from nitinol sheet or tube stock.

Figure 3B:
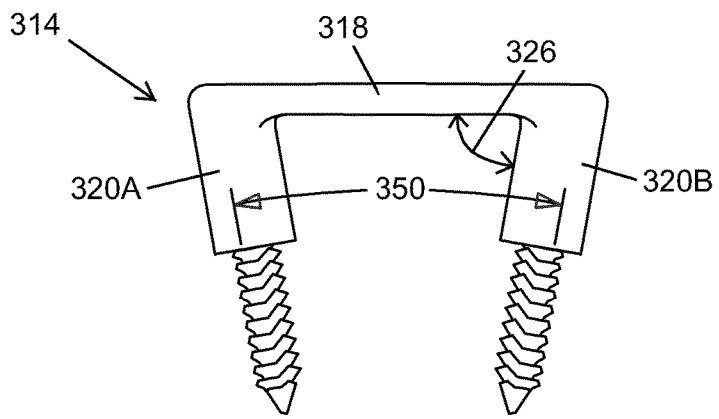
FIG. 3B is a simplified front view of the surgical staple of FIG. 3A, wherein the surgical staple is in a relaxed configuration.
Figures 3C, 3D:
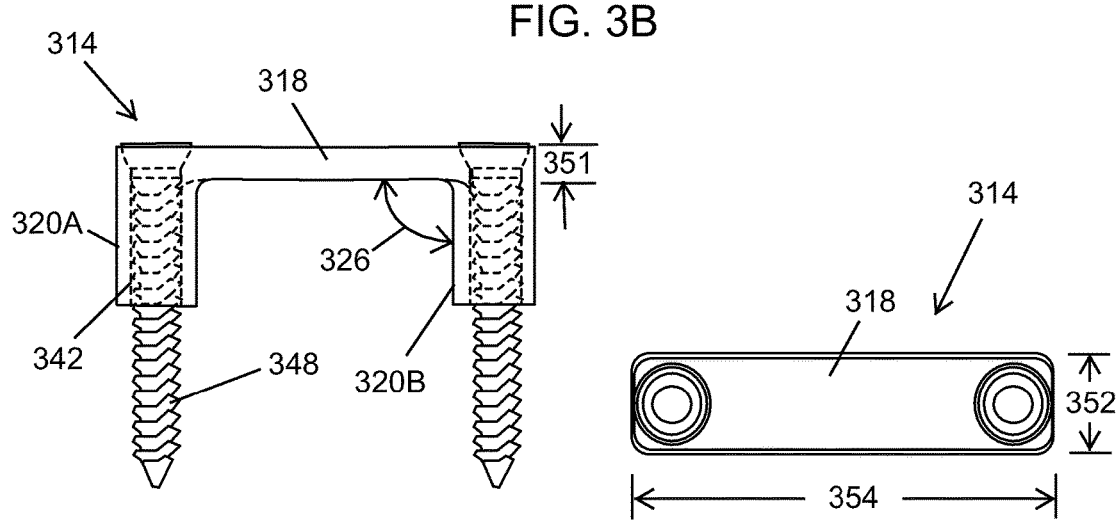
FIG. 3C is a simplified front view of the surgical staple of FIG. 3A, wherein the surgical staple is in an opened configuration.
FIG. 3D is a simplified top view of the surgical staple of FIG. 3A.

FIG. 3B is a simplified front view of the surgical staple 314 of FIG. 3A, wherein the surgical staple 314 is in the relaxed configuration. In particular, FIG. 3B illustrates that when the surgical staple 314 is in the relaxed configuration, each of the side sections 320A, 320B can cantilever away from the middle section 318 at a leg angle 326 that is less than ninety degrees. In particular, in certain embodiments, the side sections 320A, 320B can cantilever away from the middle section 318 at a leg angle 326 of between approximately 75.0 and 85.0 degrees. For example, in certain non-exclusive alternative embodiments, the leg angle 326 between the side sections 320A, 320B and the middle section 318 can be approximately 75.0, 77.0, 79.0, 80.0, 81.0, 83.0 or 85.0 degrees. Alternatively, the leg angle 326 can be greater than 85.0 degrees, less than 75.0 degrees, or another value between 75.0 and 85.0 degrees.

It should be noted that, as with the previous embodiment, the leg angle 326 between one side section 320A and the middle section 318 can be substantially the same as or can be different than the leg angle 326 between the other side section 320B and the middle section 310. Thus, FIG. 3B further illustrates a flex angle 350 that shows the angle of one side section 320A relative to the other side section 320B. In certain embodiments, the flex angle 350 can be between approximately 15.0 and 25.0 degrees. For example, in some non-exclusive alternative embodiments, the flex angle 350 can be approximately 15.0, 17.0, 19.0, 20.0, 21.0, 23.0 or 25.0 degrees. Alternatively, the flex angle 350 can be greater than 25.0 degrees, less than 15.0 degrees, or some other value between 15.0 and 25.0 degrees.

FIG. 3C is a simplified front view of the surgical staple 314 of FIG. 3A, wherein the surgical staple 314 is in the opened configuration. In particular, FIG. 3C illustrates the surgical staple 314 after the surgical staple 314 has been moved to the opened configuration in any suitable manner, e.g., manually, automatically, and/or with the use of a tool. When the surgical staple 214 is in the opened configuration, the side sections 320A, 320B can cantilever away from the middle section 318 at a leg angle 326 of closer to or approximately ninety degrees, such that the surgical staple 314 can be quickly and easily inserted into the holes 16 (illustrated in FIG. 1) that have been created in the bone parts 10, 12 (illustrated in FIG. 1) to specifically receive the surgical staple 314. For example, in certain applications, when the surgical staple 314 is in the opened configuration, each of the side sections 320A, 320B can cantilever away from the middle section 318 at a leg angle 326 of approximately 95.0, 94.0, 93.0, 92.0, 91.0, 90.0, 89.0, 88.0, 87.0, 86.0, or 85.0 degrees. Alternatively, the leg angle 326 in the opened configuration can be greater than 95.0 degrees, less than 85.0 degrees, or some other value between 85.0 and 95.0 degrees.

Additionally, FIG. 3C further illustrates how the screw apertures 342 (illustrated in phantom) extend fully through each of the side sections 320A, 320B to enable the screws 348 to be threaded and/or extended fully through the side sections 320A, 320B. As noted above, with this design, the side sections 320A, 320B can extend part way into the depth of the holes 16 in the bone parts 10, 12, and the screws 348 can be threaded further into the holes 16 in the bone parts 10, 12 so that the surgical staple 314 is more securely retained within the holes 16 in the bone parts 10, 12.

Further, FIG. 3C also illustrates a plate thickness 351 of the middle section 318. In some embodiments, the plate thickness 351 can be between approximately 1.0 and 2.0 millimeters. For example, in certain non-exclusive alternative embodiments, the plate thickness 351 can be approximately 1.0, 1.2, 1.4, 1.5, 1.6, 1.8 or 2.0 millimeters. Alternatively, the plate thickness 351 can be greater than 2.0 millimeters, less than 1.0 millimeters, or some other value between 1.0 and 2.0 millimeters.

FIG. 3D is a simplified top view of the surgical staple 314 of FIG. 3A. In particular, FIG. 3D illustrates certain design aspects of the middle section 318 of the surgical staple 314. As illustrated, in some embodiments, the middle section 318 can be a substantially rectangular-shaped plate having a plate width 352 and a plate length 354. In some such embodiments, the middle section 318 can have a plate width 352 of between approximately 2.0 millimeters and 6.0 millimeters, and the middle section 318 can have a plate length 354 of between approximately 7.0 millimeters and 15.0 millimeters. For example, in certain non-exclusive alternative embodiments, the plate width 352 can be approximately 2.0, 2.5, 3.0, 3.5, 4.0, 4.5, 5.0, 5.5 or 6.0 millimeters, and the plate length 354 can be approximately 7.0, 8.0, 9.0, 10.0, 11.0, 12.0, 13.0, 14.0 or 15.0 millimeters. Alternatively, the plate width 352 can be greater than 6.0 millimeters, less than 2.0 millimeters, or some other value between 2.0 and 6.0 millimeters; and/or the plate length 354 can be greater than 15.0 millimeters, less than 7.0 millimeters, or some other value between 7.0 and 15.0 millimeters. Still alternatively, the middle section 318 can be other than substantially rectangular-shaped.

FIG. 4A is a simplified front view of still another embodiment of a surgical staple 414 having features of the present invention. As illustrated, the surgical staple 414 is somewhat similar to the surgical staple 214 illustrated and described above in relation to FIGS. 2A-2E. For example, the surgical staple 414 again includes a middle section 418 and two side sections 420A, 420B that cantilever away from the middle section 418. Additionally, the surgical staple 414 can again be selectively movable between a relaxed configuration and an opened configuration (not illustrated). In particular, as illustrated in FIG. 4A, the surgical staple 414 is in the relaxed configuration, such that the side sections 420A, 420B cantilever away from the middle section 418 at a leg angle 426 of less than ninety degrees. Moreover, as shown, with this design the side sections 420A, 420B are angled slightly toward one another.

Further, as illustrated in FIG. 4A, the surgical staple 414 again includes a plurality of teeth 424 that are fixedly secured to and/or integrally formed with each of the side sections 420A, 420B. As with the previous embodiment, the teeth 424 are sized and shaped to enable easy insertion of the surgical staple 414 into the holes 16 (illustrated in FIG. 1) in the bone parts 10, 12 (illustrated in FIG. 1), while inhibiting removal of the surgical staple 414 from the holes 16 in the bone parts 10, 12 after insertion.

However, in the embodiment illustrated in FIG. 4A, the middle section 418 has a different design. In particular, as illustrated, the middle section 418 has a stepped design wherein a first middle portion 418A is coupled to and offset from a second middle portion 418B. Stated in another manner, the first middle portion 418A is stepped down relative to the second middle portion 418B. The offset between the first middle portion 418A and the second middle portion 418B can be described and/or defined in terms of an offset distance 456 and/or an offset angle 458.

In certain embodiments, the first middle portion 418A can be offset from the second middle portion 418B by an offset distance 456 of between approximately 2.0 millimeters and 9.0 millimeters. For example, in certain non-exclusive alternative embodiments, the offset distance 456 between the first middle portion 418A and the second middle portion 418B can be approximately 2.0, 3.0, 4.0, 5.0, 6.0, 7.0, 8.0 or 9.0 millimeters. Alternatively, the offset distance 456 between the first middle portion 418A and the second middle portion 418B can be greater than 9.0 millimeters, less than 2.0 millimeters, or some other value between 2.0 and 9.0 millimeters.

Additionally, in certain embodiments, the offset angle 458 between the first middle portion 418A and the second middle portion 418B can be between approximately thirty and eighty degrees. For example, in certain non-exclusive alternative embodiments, the offset angle 458 between the first middle portion 418A and the second middle portion 418B can be approximately, thirty, thirty-five, forty, forty-five, fifty, fifty-five, sixty, sixty-five, seventy, seventy-five or eighty degrees. Alternatively, the offset angle 458 can be greater than eighty degrees, less than thirty degrees, or some other value between thirty and eighty degrees.

The surgical staple 414 illustrated in FIG. 3A can be utilized for various purposes where a step displacement exists between two bone pieces. For example, one possible application for the surgical staple 414 is during repair of the calcaneus (or heel bone) of the foot. In particular, the surgical staple 414 can be utilized to hold a calcaneal slide. During a procedure related to the calcaneus, alignment in the hind-foot can be corrected by resecting and displacing the two resected pieces of the calcaneus. This corrective resection causes a step displacement between the two resected pieces of the calcaneus that generally ranges from two millimeters to nine millimeters, although different step displacements are also possible. Thereafter, the surgical staple 414 can be used to hold the two displaced pieces of the calcaneus in place while healing.

Further, as illustrated in FIG. 4A, the second side section 420B has a leg length 428 that can be varied depending on the desired usage of the surgical staple 414. In some embodiments, the second side section 420B can have a leg length 428 of between approximately 16.0 and 24.0 millimeters. For example, in certain non-exclusive alternative embodiments, the leg length 428 of the second side section 420B can be approximately 16.0, 17.0, 18.0, 19.0, 20.0, 21.0, 22.0, 23.0 or 24.0 millimeters. Alternatively, the leg length 428 of the second side section 420B can be greater than 24.0 millimeters, less than 16.0 millimeters, or some other value between 16.0 and 24.0 millimeters.

It should be noted that, in different embodiments, the first side section 420A can have a length that is substantially equal to or different than the leg length 428 of the second side section 420B.

FIG. 4B is a simplified top view of the surgical staple 414 of FIG. 4A. FIG. 4B illustrates certain additional features of this embodiment of the surgical staple 414. For example, as shown in FIG. 4B, the surgical staple 414 has a staple width 430 that can be substantially equal to the leg length 428 (illustrated in FIG. 2A). In certain embodiments, the surgical staple 414 can have a staple width 430 of between approximately 16.0 and 24.0 millimeters. For example, in certain non-exclusive alternative embodiments, the staple width 430 can be approximately 16.0, 17.0, 18.0, 19.0, 20.0, 21.0, 22.0, 23.0 or 24.0 millimeters. Alternatively, the staple width 430 can be greater than 24.0 millimeters, less than 16.0 millimeters, or some other value between 16.0 and 24.0 millimeters.

FIG. 4C is a sectional view of the surgical staple 414 taken on line C-C in FIG. 4A. In particular, FIG. 4C illustrates still further details of the surgical staple 414. For example, FIG. 2C illustrates that the end 422 of the side sections (only the first side section 420A is illustrated in FIG. 4C) flares outwardly slightly relative to the majority of the side section 420A. Stated in another manner, the side section 420A has a wider end 422 (or foot) design that enables the side section 420A to fill the hole 16 (illustrated in FIG. 1) more completely in the bone part, e.g., the first bone part 10 or the second bone part 12 illustrated in FIG. 1. Moreover, as noted above, such design further enables better force distribution against the bone part 10, 12, and greater movement of the bone part 10, 12, which, in turn, result in better bone to bone compression.

Further, FIG. 4C also illustrates the general shape of the teeth 424 that are fixedly secured to and/or integrally formed with each of the side sections 420A. For example, as shown in FIG. 4C, each of the teeth 424 again tapers inwardly toward the top of the tooth 424.

FIG. 4D is an enlarged view of a portion of the surgical staple 414 as indicated by circle and arrows D-D in FIG. 4A. In particular, FIG. 4D more clearly illustrates certain design aspects of the teeth 424 that are fixedly secured to and/or integrally formed with the side section 420A. For example, FIG. 4D illustrates a tooth height 436, a tooth depth 438 and a tooth angle 440 of the teeth 424.

In certain embodiments, the tooth height 436 can be between approximately 1.00 and 1.30 millimeters. For example, in certain non-exclusive alternative embodiments, the tooth height 436 can be approximately 1.00, 1.05, 1.10, 1.15, 1.20, 1.25 or 1.30 millimeters. Alternatively, the tooth height 436 can be greater than 1.30 millimeters, less than 1.00 millimeters, or some other value between 1.00 and 1.30 millimeters.

Additionally, in certain embodiments, the tooth depth 438 can be between approximately 0.40 and 0.60 millimeters. For example, in certain non-exclusive alternative embodiments, the tooth depth 438 can be approximately 0.40, 0.45, 0.50, 0.55 or 0.60 millimeters. Alternatively, the tooth depth 438 can be greater than 0.60 millimeters, less than 0.40 millimeters, or some other value between 0.40 and 0.60 millimeters.

Further, in certain embodiments, the tooth angle 440 can be between approximately 55.0 and 75.0 degrees. For example, in certain non-exclusive alternative embodiments, the tooth angle 440 can be approximately 55.0, 57.5, 60.0, 62.5, 65.0, 67.5, 70.0, 72.5 or 75.0 degrees. Alternatively, the tooth angle 440 can be greater than 75.0 degrees, less than 55.0 degrees, or some other value between 55.0 and 75.0 degrees.

Still further, FIG. 4D also illustrates that the end 422 of the side section 420A can be narrower in cross-section than the majority of the side section 420A to better enable insertion of the surgical staple 414 into the bone parts 10, 12 (illustrated in FIG. 1).

Figure 5B:
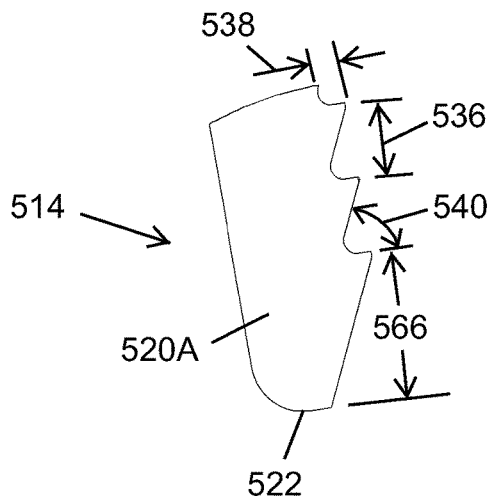
FIG. 5B is an enlarged view of a portion of the surgical staple as indicated by circle and arrows B-B in FIG. 5A.
Figure 5A:
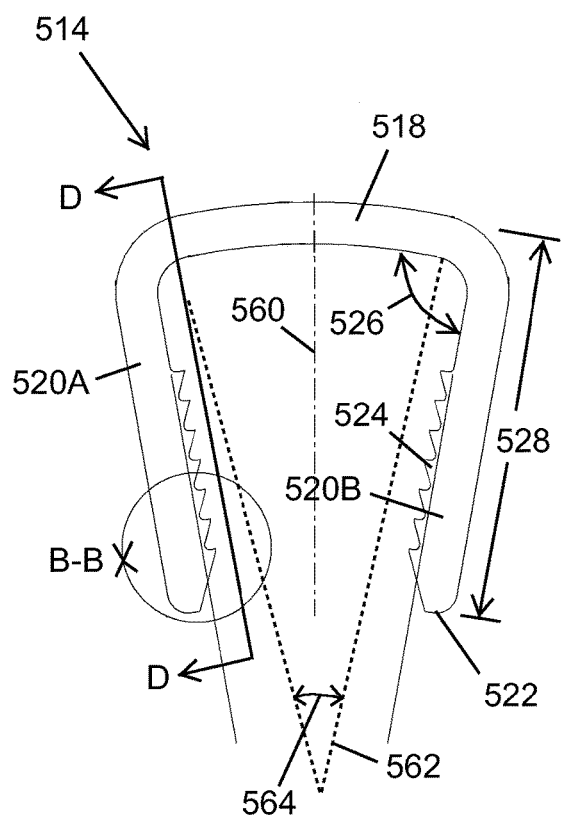
FIG. 5A is a simplified front view of yet another embodiment of a surgical staple having features of the present invention.

FIG. 5A is a simplified front view of yet another embodiment of a surgical staple 514 having features of the present invention. Moreover, it should be noted that the surgical staple 514 is illustrated in the relaxed configuration. As illustrated, the surgical staple 514 is substantially similar to the surgical staples 214, 414 illustrated and described above in relation to FIGS. 2A-2E and FIGS. 4A-4D, respectively. For example, as shown in FIG. 5A, the surgical staple 514 is again somewhat horseshoe shaped, including a middle section 518 and two side sections 520A, 520B that cantilever away from the middle section 518. Additionally, when in the relaxed configuration, each of the side sections 520A, 520B can cantilever away from the middle section 518 at a leg angle 526 of less than ninety degrees such that the side sections 520A, 520B are angled slightly toward one another. Further, each side section 520A, 520B again has an end 522 that is somewhat tapered such that the end 522 is narrower in cross-section than the majority of the side section 520A, 520B to better enable insertion of the surgical staple 514.

Still further, each side section 520A, 520B can again include a plurality of teeth 524 that are angled so as to enable easy insertion of the surgical staple 514 into the holes 16 (illustrated in FIG. 1) in the bone parts 10, 12 (illustrated in FIG. 1), while inhibiting removal of the surgical staple 514 from the holes 16 in the bone parts 10, 12.

However, in this embodiment, the middle section 518 has a different design. In particular, as shown in FIG. 5A, the middle section 518 is somewhat curved or arched, i.e. about a staple axis 560. The curvature of the middle section 518 can be described and/or defined in terms of a radius of curvature 562 (illustrated by a dotted line) and/or an angle of curvature 564.

In certain embodiments, the middle section 518 can have a radius of curvature 562 that is between approximately 25.0 and 95.0 millimeters. For example, in certain non-exclusive alternative embodiments, the middle section 518 can have a radius of curvature 562 of approximately 25.0, 30.0, 35.0, 40.0, 45.0, 50.0, 55.0, 60.0, 65.0, 70.0, 75.0, 80.0, 85.0, 90.0 or 95.0 millimeters. Alternatively, the middle section 518 can have a radius of curvature 562 of greater than 95.0 millimeters, less than 25.0 millimeters, or another value between 25.0 and 95.0 millimeters.

Additionally, in certain embodiments, the middle section 518 can have an angle of curvature 564 that is between approximately 15.0 and 35.0 degrees. For example, in certain non-exclusive alternative embodiments, the middle section 518 can have an angle of curvature 564 of approximately 15.0, 17.5, 20.0, 22.5, 25.0, 27.5, 30.0, 32.5 or 35.0 degrees. Alternatively, the middle section 518 can have an angle of curvature 564 of greater than 35.0 degrees, less than 15.0 degrees, or another value between 15.0 and 35.0 degrees.

Further, as illustrated in FIG. 5A, the side sections 520A, 520B have a leg length 528 that can be varied depending on the desired usage of the surgical staple 514. In some embodiments, the side sections 520A, 520B can have a leg length 528 of between approximately 15.0 and 22.0 millimeters. For example, in certain non-exclusive alternative embodiments, the leg length 528 of the side sections 520A, 520B can be approximately 15.0, 16.0, 17.0, 18.0, 19.0, 20.0, 21.0 or 22.0 millimeters. Alternatively, the leg length 528 of the side sections 520A, 520B can be greater than 22.0 millimeters, less than 15.0 millimeters, or some other value between 15.0 and 22.0 millimeters.

FIG. 5B is an enlarged view of a portion of the surgical staple 514 as indicated by circle and arrows B-B in FIG. 5A. In particular, FIG. 5B more clearly illustrates certain design aspects of the teeth 524 that are fixedly secured to and/or integrally formed with the side sections 520A. For example, FIG. 5B illustrates a tooth height 536, a tooth depth 538 and a tooth angle 540 of the teeth 524.

In certain embodiments, the tooth height 536 can again be between approximately 1.00 and 1.30 millimeters, although different values for the tooth height 536 are also possible. Additionally, in certain embodiments, the tooth depth 538 can again be between approximately 0.40 and 0.60 millimeters, although different values for the tooth depth 538 are also possible. Further, in certain embodiments, the tooth angle 540 can again be between approximately 55.0 and 75.0 degrees, although different values for the tooth angle 540 are also possible.

Additionally, as illustrated in FIG. 5B, the tooth 524 nearest the end 522 of the side section 520A can be positioned at an initial tooth distance 566 of between approximately 2.00 and 2.50 millimeters from the end 522 of the side section 520A. For example, in certain non-exclusive alternative embodiments, the initial tooth distance 566 can be approximately 2.00, 2.05, 2.10, 2.15, 2.20, 2.25, 2.30, 2.35, 2.40, 2.45 or 2.50 millimeters. Alternatively, the initial tooth distance 566 can be greater than 2.50 millimeters, less than 2.00 millimeters, or some other value between 2.00 and 2.50 millimeters.

Figure 5C:
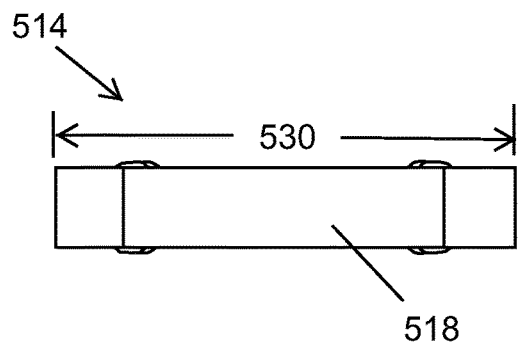
FIG. 5C is a simplified top view of the surgical staple of FIG. 5A.

FIG. 5C is a simplified top view of the surgical staple 514 of FIG. 5A. FIG. 5C illustrates certain additional features of this embodiment of the surgical staple 514 from the perspective of looking down on the middle section 518 of the surgical staple 514. For example, as shown in FIG. 5C, the surgical staple 514 has a staple width 530 that can be between approximately 15.0 and 25.0 millimeters. For example, in certain non-exclusive alternative embodiments, the staple width 530 can be approximately 15.0, 16.0, 17.0, 18.0, 19.0, 20.0, 21.0, 22.0, 23.0, 24.0 or 25.0 millimeters. Alternatively, the staple width 530 can be greater than 25.0 millimeters, less than 15.0 millimeters, or some other value between 15.0 and 25.0 millimeters.

Figure 5D:
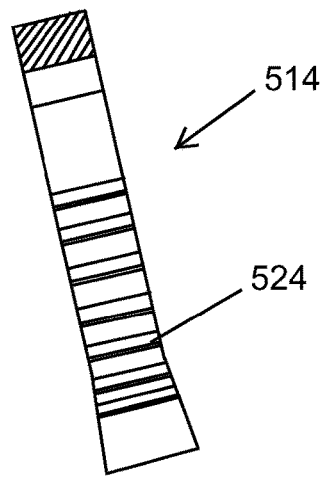
FIG. 5D is a sectional view of the surgical staple taken on line D-D in FIG. 5A.

FIG. 5D is a sectional view of the surgical staple 514 taken on line D-D in FIG. 5A. In particular, FIG. 5D illustrates still further details of the surgical staple 514. More specifically, FIG. 5D illustrates certain details of the teeth 524 that may be included as part of the surgical staple 514.

Figure 6:
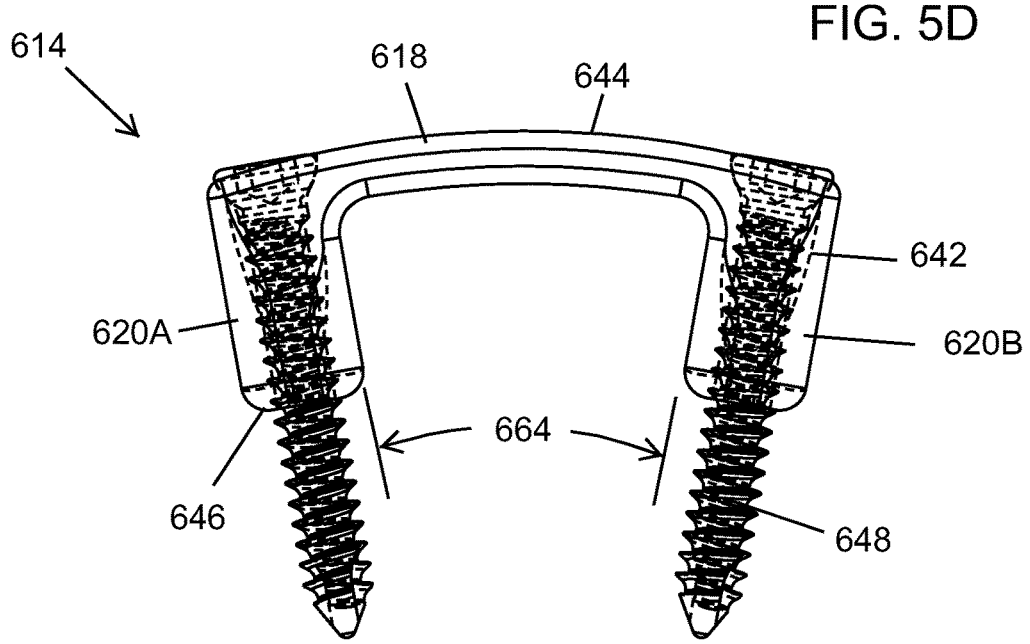
FIG. 6 is a simplified front view of still another embodiment of a surgical staple having features of the present invention.

FIG. 6 is a simplified front view of still another embodiment of a surgical staple 614 having features of the present invention. It should be noted that the surgical staple 614 is illustrated in the relaxed configuration. As illustrated, the surgical staple 614 is substantially similar to the surgical staple 314 illustrated and described above in relation to FIGS. 3A-3D. For example, the surgical staple 614 again includes a resilient, plate-shaped middle section 618 and two side sections 620A, 620B that cantilever away from the middle section 618. More specifically, when the surgical staple 614 is in the relaxed configuration, the side sections 620A, 620B can again cantilever away from the middle section 618 such that the side sections 618 are angled slightly toward one another. Alternatively, in one embodiment, in the open configuration, the middle section 618 is generally flat with the side sections 620A, 620B substantially normal to the middle section 618.

Additionally, in this embodiment, the surgical staple 614 again includes a pair of screw apertures 642 (illustrated in phantom) that extend through a top surface 644 of the middle section 618 of the surgical staple 614 and through the length of the side sections 620A, 620B such that the screw aperture 642 extends through an end 646 of the side section 620A, 620B away from the middle section 618. Each of the screw apertures 642 is again adapted to receive a screw 648 that is designed to be inserted into one of the holes 16 (illustrated in FIG. 1) in the bone parts 10, 12 (illustrated in FIG. 1).

Additionally, in some embodiments, the side sections 620A, 620B can also include one or more teeth (not illustrated) that are fixedly secured to and/or integrally formed with each of the side sections 620A, 620B.

However, in this embodiment, the middle section 618 has a different design. In particular, as shown in FIG. 6, in the relaxed configuration, the middle section 618 is somewhat curved or arched. Similar to the embodiment illustrated in FIGS. 5A-5D, the curvature of the middle section 618 can be described and/or defined in terms of a radius of curvature (not illustrated in FIG. 6) and/or an angle of curvature 664. In certain embodiments, the angle of curvature 664 of the middle section 618 can be approximately equal to the angle of the side sections 620A, 620B relative to one another. In some non-exclusive alternative embodiments, the angle of curvature 664 can be between approximately 16.0 degrees and 24.0 degrees. Alternatively, the angle of curvature 664 can be greater than 24.0 degrees or less than 16.0 degrees.

Alternatively, in the open configuration, the resilient middle section 618 is deformed to be generally flat, with the side sections 620A, 620B and screws 648 being substantially normal to the middle section 618. With this design, with the middle section 618 held in the open configuration with an insertion tool (not shown), the screws 648 can be easily inserted into the bone parts 10, 12 (illustrated in FIG. 1). The threads of the screws 648 will engage and retain the bone parts 10, 12. Subsequently, upon release of the middle section 618 with the tool, the resilient middle section 618, that is biased to return to the relaxed configuration, will urge the bone parts 10, 12 together.

Figure 7A:
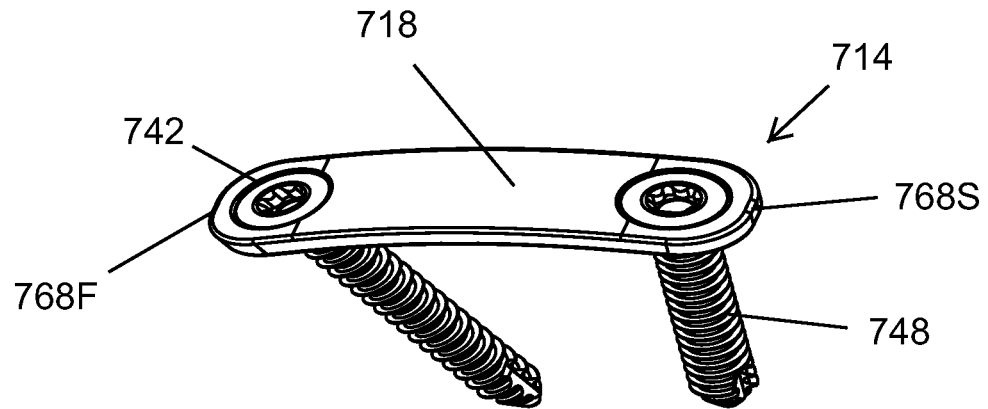
FIG. 7A is a simplified perspective view of still yet another embodiment of a surgical staple having features of the present invention.

FIG. 7A is a simplified perspective view of still yet another embodiment of a surgical staple 714 having features of the present invention. The surgical staple is again selectively movable between a relaxed configuration (as shown in FIG. 7A) and an opened configuration (not illustrated). As illustrated, the surgical staple 714 is somewhat similar to the surgical staple 614 illustrated and described above in relation to FIG. 6. For example, the surgical staple 714 again includes a plate-shaped middle section 718 that is somewhat curved or arched.

Additionally, in this embodiment, the surgical staple 714 again includes a pair of screw apertures 742 that extend through the middle section 718 of the surgical staple 714. As illustrated, one of the screw apertures 742 is positioned substantially near or adjacent to a first end 768F of the middle section 718, and the other screw aperture 742 is positioned substantially near or adjacent to a second end 768S of the middle section 718. Alternatively, the screw apertures 742 can be positioned within a different portion of the middle section 718 than specifically illustrated in FIG. 7A. Each of the screw apertures 742 is again adapted to receive a screw 748 that is designed to be inserted into one of the holes 16 (illustrated in FIG. 1) in the bone parts 10, 12 (illustrated in FIG. 1).

However, in this embodiment, the surgical staple 714 is designed without side sections that cantilever away from the middle section 718. Stated in another manner, the surgical staple 714 includes only the middle section 718 and the screws 748 that extend through the screw apertures 742. Further, when the surgical staple 714 is in the relaxed configuration, as the screws 748 extend through and away from the middle section 718, the screws 748 are angled slightly toward one another.

Figure 7B:
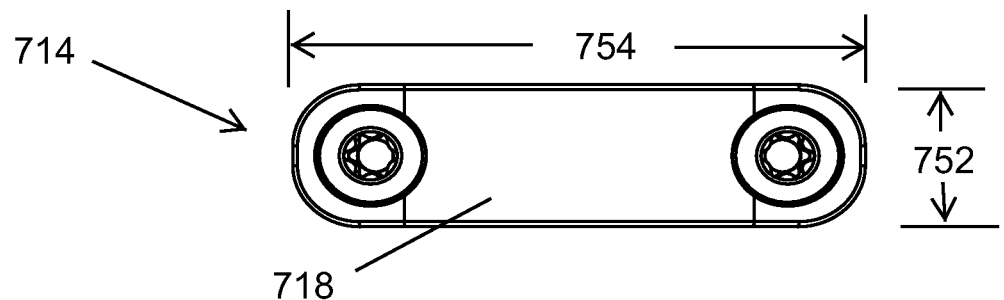
FIG. 7B is a simplified top view of the surgical staple of FIG. 7A.

FIG. 7B is a simplified top view of the surgical staple 714 of FIG. 7A. As illustrated, in some embodiments, the middle section 718 of the surgical staple 714 can be a substantially rectangular-shaped plate having a plate width 752 and a plate length 754. In some such embodiments, the middle section 718 can have a plate width 752 of between approximately 6.0 and 8.5 millimeters, and the middle section 718 can have a plate length 754 of between approximately 15.0 and 50.0 millimeters. Alternatively, the plate width 752 can be greater than 8.5 millimeters or less than 6.0 millimeters, and/or the plate length 754 can be greater than 50.0 millimeters or less than 15.0 millimeters. Still alternatively, the middle section 718 can be other than substantially rectangular-shaped.

Figure 7C:
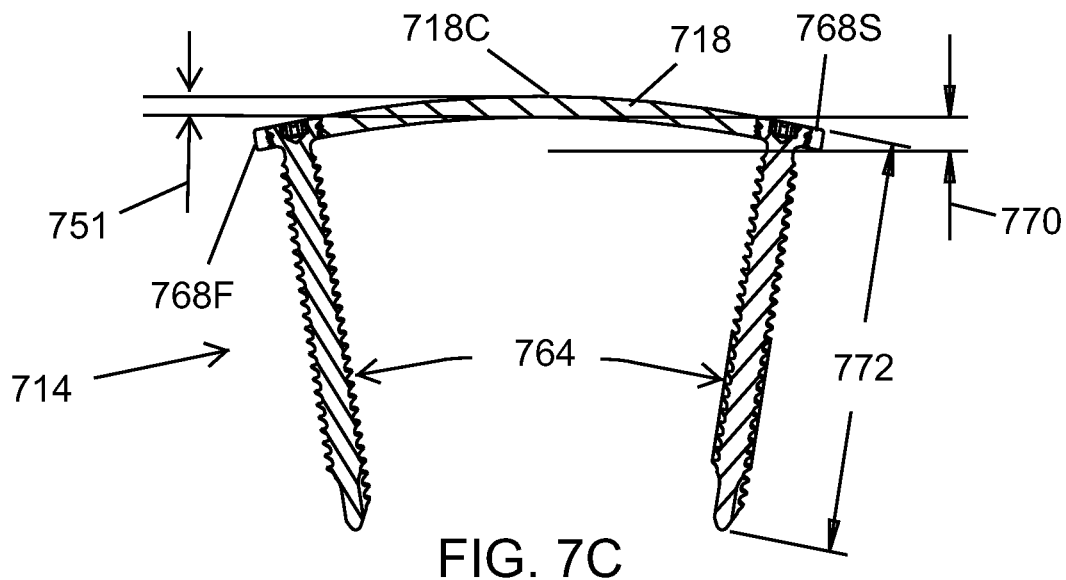
FIG. 7C is a sectional view of the surgical staple taken on line C-C in FIG. 7B.

FIG. 7C is a sectional view of the surgical staple 714 taken on line C-C in FIG. 7B. In particular, FIG. 7C illustrates the curvature of the middle section 718 in greater detail. Similar to the embodiment illustrated in FIG. 6, the curvature of the middle section 718 can be described and/or defined in terms of a radius of curvature (not illustrated) and/or an angle of curvature 764. In certain embodiments, the angle of curvature 764 can be between approximately 16.0 degrees and 26.0 degrees. For example, in certain non-exclusive alternative embodiments, the angle of curvature 764 can be approximately 16.0, 17.0, 18.0, 19.0, 20.0, 21.0, 22.0, 23.0, 24.0, 25.0 or 26.0 degrees. Alternatively, the angle of curvature 764 can be greater than 26.0 degrees, less than 16.0 degrees, or some other value between 16.0 and 26.0 degrees.

Additionally, FIG. 7C also illustrates a plate deflection 770 of the middle section 718. The plate deflection 770 is the distance the middle section arcs or deflects downward from a center 718C of the middle section 718 to an end, i.e. the first end 768F or the second end 768S, of the middle section 718 when the middle section 718 is in the relaxed configuration. In some non-exclusive embodiments, the plate deflection 770 of the middle section 718 can be between approximately 2.0 millimeters and 3.0 millimeters. For example, in certain non-exclusive alternative embodiments, the plate deflection 770 can be approximately 2.0, 2.2, 2.4, 2.5, 2.6, 2.8 or 3.0 millimeters. Alternatively, the plate deflection 770 can be greater than 3.0 millimeters, less than 2.0 millimeters, or some other value between 2.0 and 3.0 millimeters.

Further, FIG. 7C also illustrates a plate thickness 751 of the middle section 718. In some embodiments, the plate thickness 751 can be between approximately 1.0 and 2.0 millimeters. For example, in certain non-exclusive alternative embodiments, the plate thickness 751 can be approximately 1.0, 1.2, 1.4, 1.5, 1.6, 1.8 or 2.0 millimeters. Alternatively, the plate thickness 751 can be greater than 2.0 millimeters, less than 1.0 millimeters, or some other value between 1.0 and 2.0 millimeters.

Still further, FIG. 7C also illustrates a screw length 772. The screw length 772O can vary depending on the specific requirements of the surgical staple 714. In certain embodiments, the screw length 772 can be between approximately 20.0 and 35.0 millimeters. For example, in certain non-exclusive alternative embodiments, the screw length 772 can be approximately 20.0, 22.5, 25.0, 27.5, 30.0, 32.5 or 35.0 millimeters Alternatively, the screw length 772 can be greater than 35.0 millimeters, less than 20.0 millimeters, or some other value between 20.0 and 35.0 millimeters.

In one embodiment, in the open configuration, the resilient middle section 718 is deformed to be generally flat, with the screws 748 being substantially normal to the middle section 718. With this design, with the middle section 718 held in the open configuration with an insertion tool (not shown), the screws 748 can be easily inserted into the bone parts 10, 12 (illustrated in FIG. 1). The threads of the screws 748 will engage and retain the bone parts 10, 12. Subsequently, upon release of the middle section 718 with the tool, the resilient middle section 718, that is biased to return to the relaxed configuration, will urge the bone parts 10, 12 together.

The various designs and embodiments of a surgical staple 14 illustrated and described herein can be effectively utilized for one or more of the reasons cited to herein above. For example, the surgical staples 14 having features of the present invention can be effectively utilized (i) for closure of the skin in a wide variety of surgical procedures; (ii) to move and/or maintain bones or bone parts substantially adjacent to one another after certain surgical procedures; and/or (iii) to compress and hold together in place two displaced pieces of bone while healing. Further, any of the embodiments of the surgical staple 14 illustrated and described herein can be made from a nitinol superelastic material or another appropriately resilient, flexible and/or elastic material. Additionally and/or alternatively, the surgical staples 14 can be utilized for other suitable purposes.

While a number of exemplary aspects and embodiments of a surgical staple 14 have been shown and disclosed herein above, those of skill in the art will recognize certain modifications, permutations, additions and sub-combinations thereof. It is therefore intended that the surgical staple 14 shall be interpreted to include all such modifications, permutations, additions and sub-combinations as are within their true spirit and scope, and no limitations are intended to the details of construction or design herein shown.

What is claimed is:

1. A surgical staple for inserting into one or more bone parts, the surgical staple being selectively movable between a relaxed configuration and an opened configuration, the surgical staple comprising:
    a middle section having a first end and an opposed second end, the middle section comprising a first middle portion having a first bottom surface and a second middle portion having a second bottom surface, wherein the first bottom surface and the second bottom surface are offset from one another in a direction perpendicular to the first bottom surface by an offset distance, wherein the first bottom surface and the second bottom surface are substantially parallel, wherein a first side section extends from the first end and a second side section extends from the second end, wherein the first and second side sections cantilever away from the middle section, wherein a first aperture extends through the first end and the first side section and a second aperture extends through the second end and the second side section, wherein the first aperture extends from a top surface of the first middle portion to the bottom surface of the first side section and the second aperture extends from a top surface of the second middle portion to a bottom surface of the second side section, and wherein the first side section is at least partially inserted into a first bone section and the second side section is at least partially inserted into a second bone section;
    a first screw that extends through the first aperture and extends a predetermined distance from the bottom surface of the first side section to directly interface with the first bone section; and
    a second screw that extends through the second aperture and extends a predetermined distance from the bottom surface of the second side section to directly interface with the second bone section, wherein the first screw and the second screw are angled toward one another when the surgical staple is in the relaxed configuration, and wherein the direct interfacing of the first side section and first screw and the second side section and second screw with respective first and second bone sections couples the surgical staple to the first and second bone sections.

2. The surgical staple of claim 1 wherein the offset distance is between approximately 2.0 and 9.0 mm.

3. The surgical staple of claim 1 wherein an angled portion is disposed between the first middle portion and the second middle portion, and wherein the angled portion defines an angle with respect to the second bottom surface of between approximately 30.0 and 80.0 degrees.

4. The surgical staple of claim 1 wherein the first side section and the second side section are angled toward one another when the surgical staple is in the relaxed configuration.

5. The surgical staple of claim 4 wherein the first side section cantilevers away from the middle section at a leg angle of between approximately 75.0 and 85.0 degrees when the surgical staple is in the relaxed configuration.

6. The surgical staple of claim 1 wherein the middle section is made from a resilient material.

7. A surgical staple for inserting into one or more bone parts, the surgical staple being selectively movable between a relaxed configuration and an opened configuration, the surgical staple comprising:
    a middle section comprising a first middle portion having a first bottom surface and a second middle portion having a second bottom surface, wherein the first bottom surface and the second bottom surface are offset from one another in a direction perpendicular to the first bottom surface by an offset distance, and wherein the first bottom surface and the second bottom surface are substantially parallel;
    a first side section that cantilevers away from the first middle portion, the first side section including an upper portion that is positioned substantially adjacent to the first middle portion and an end that is positioned away from the first middle portion, and wherein the first side section is inserted into a first bone section, wherein the first middle portion of the middle section and the first side section define a first aperture extending from a top surface of the first middle portion to the end of the first side section, and wherein the first aperture is sized and configured to receive a first screw therethrough such that the first screw extends through the first aperture and extends through the first side section to directly interface with the first bone section; and
    a second side section that cantilevers away from the second middle portion, the second side section including an upper portion that is positioned substantially adjacent to the second middle portion and an end that is positioned away from the second middle portion, and wherein the end is inserted into a second bone section.

8. The surgical staple of claim 7 wherein the end of the first side section is at least fifteen percent wider than the upper portion of the first side section and the end of the second side section is at least approximately fifteen percent wider than the upper portion of the second side section.

9. The surgical staple of claim 7 wherein the middle section includes a first end and an opposed second end, wherein the first side section cantilevers away from the middle section near the first end, and wherein the second side section cantilevers away from the middle section near the second end.

10. The surgical staple of claim 9 wherein the first side section and the second side section are angled toward one another when the surgical staple is in the relaxed configuration, and wherein the first side section and the second side section are substantially normal to the middle section in the opened configuration.

11. The surgical staple of claim 10 wherein the first side section cantilevers away from the middle section at a leg angle of between approximately 75.0 and 85.0 degrees when the surgical staple is in the relaxed configuration.

12. The surgical staple of claim 9, wherein the second middle portion includes a second aperture that is positioned near the second end, wherein the second aperture extends from a top surface of the second middle portion through a length of the second side section to the end of the second side section, wherein the second aperture is sized and configured to receive a second screw that extends through the second end and the second side section to directly interface the second bone section.

13. The surgical staple of claim 7 further comprising a plurality of teeth integrally formed with the first side section and the second side section.

14. The surgical staple of claim 7 wherein the middle section and the first side section are made from a resilient material.

15. The surgical staple of claim 7 wherein the offset distance is between approximately 2.0 and 9.0 mm.

16. The surgical staple of claim 7 wherein an angled portion is disposed between the first middle portion and the second middle portion, and wherein the angled portion defines an angle with respect to the second bottom surface of between approximately 30.0 and 80.0 degrees.

17. The surgical staple of claim 7 wherein the first side section and the second side section are different lengths.

18. A method for compressing a first bone part and a second bone part, the method comprising the steps of:
   positioning a middle section of a surgical staple substantially adjacent to at least one of the first bone part and the second bone part, the middle section having a first end and an opposed second end, the middle section comprising a first middle portion having a first bottom surface and a second middle portion having a second bottom surface, wherein the first bottom surface and the second bottom surface are offset from one another in a direction perpendicular to the first bottom surface by an offset distance, wherein the first bottom surface and the second bottom surface are substantially parallel, wherein a first side section extends from the first end and a second side section extends from the second end, wherein the first and second side sections cantilever away from the middle section, wherein a first aperture extends through the first end and the first side section and a second aperture extends through the second end and the second side section, wherein the first aperture extends from a top surface of the first middle portion to the bottom surface of the first side section and the second aperture extends from a top surface of the second middle portion to a bottom surface of the second side section, the surgical staple being selectively movable between a relaxed configuration and an opened configuration, and wherein the first side section is at least partially inserted into a first bone section and the second side section is at least partially inserted into a second bone section;
   extending a first screw through the first aperture to a predetermined distance from the bottom surface of the first side section and into the first bone part to directly interface with the first bone part; and
   extending a second screw through the second aperture to a predetermined distance from the bottom surface of the second side section and into the second bone part to directly interface with the second bone part, the first screw and the second screw being angled toward one another when the surgical staple is in the relaxed configuration, and wherein the direct interfacing of the first side section and first screw and the second side section and second screw into respective first and second bone sections couples the surgical staple to first and second bone sections.

19. The method of claim 18 wherein the offset distance is between approximately 2.0 and 9.0 mm.

20. The method of claim 18 wherein the first side section and the second side section are angled toward one another when the surgical staple is in the relaxed configuration, and wherein the first side section and the second side section are substantially normal to the middle section in the opened configuration.

* * * * *